United States Patent
Takizawa (10) Patent No.: US 8,036,733 B2
(45) Date of Patent: Oct. 11, 2011

(54) DIAGNOSTIC PARAMETER CALCULATION METHOD, SYSTEM FOR DIAGNOSIS AND DIAGNOSTIC PROGRAM

(76) Inventor: Kiyoshi Takizawa, Tokyo (JP)

( * ) Notice: Subject to any disclaimer, the term of this patent is extended or adjusted under 35 U.S.C. 154(b) by 821 days.

(21) Appl. No.: 11/596,981

(22) PCT Filed: May 19, 2005

(86) PCT No.: PCT/JP2005/009123
§ 371 (c)(1),
(2), (4) Date: May 12, 2008

(87) PCT Pub. No.: WO2005/112751
PCT Pub. Date: Dec. 1, 2005

(65) Prior Publication Data
US 2009/0012414 A1    Jan. 8, 2009

(30) Foreign Application Priority Data
May 20, 2004    (JP) .................... 2004-150375

(51) Int. Cl.
*A61B 5/04*    (2006.01)
(52) U.S. Cl. ...................................... 600/509
(58) Field of Classification Search .......... 600/508–528
See application file for complete search history.

(56) References Cited

U.S. PATENT DOCUMENTS

| | | | |
|---|---|---|---|
| 5,201,321 A * | 4/1993 | Fulton | 600/515 |
| 5,560,368 A | 10/1996 | Berger | |
| 5,609,158 A | 3/1997 | Chan | |
| 5,755,671 A | 5/1998 | Albrecht et al. | |
| 7,330,750 B2 * | 2/2008 | Erkkila et al. | 600/509 |
| 2003/0125632 A1 * | 7/2003 | Takizawa | 600/509 |

FOREIGN PATENT DOCUMENTS

| | | |
|---|---|---|
| JP | 06-054815 | 3/1994 |
| JP | 08-056914 | 3/1996 |
| JP | 08-322813 | 12/1996 |
| JP | 09-201344 | 8/1997 |
| JP | 10-225443 | 8/1998 |
| JP | 2003-260035 | 9/2003 |
| JP | 2004-016248 | 1/2004 |

* cited by examiner

*Primary Examiner* — Mallika Fairchild
(74) *Attorney, Agent, or Firm* — Antonelli, Terry, Stout & Kraus, LLP.

(57) ABSTRACT

A diagnostic parameter calculation method, system and program which detect symptomatically abnormal electrocardiogram data of a patient, using R-R intervals detected from electrocardiogram data collected for a patient to generate a time-series data, then generating a series of partial sets B(j)'s, each B(j) consisting of successive elements starting from the j-th element of the time-series data, and calculating characteristic quantity set (yj, xj) for each B(j), wherein yj is the mean value of all elements, and xj is the mean value of each difference of the first element from each element in the B(j), then, after splitting the (y, x)-plane into lattices, parameters u, v, w are calculated as indices for diagnosis, wherein v is the number of lattices including only one characteristic quantity set, u is the difference subtracted v from the total number of the characteristic quantity sets, and w is the maximum number of characteristic quantity sets included in a lattice.

21 Claims, 8 Drawing Sheets

Figure 8
NEW FIGURE

Table 1

| subject | age/sex | index of heart condition $\mu$ | | | number of experiments | N+1 | remarks |
|---|---|---|---|---|---|---|---|
| | | mearn | max | min | | | |
| Z1 | 88/f | 0.021 | 0.037 | 0.0045 | 12 | 36,000 | end stage of lung cancer (died) |
| Z2 | 78/f | 0.15 | 0.58 | 0.042 | 23 | 36,000 | bed ridden (aged people) |
| Z3 | 92/m | 0.21 | 0.60 | 0.024 | 47 | 36,000 | senility (died) |
| Z4 | 94/f | 0.53 | 1.76 | 0.022 | 12 | 36,000 | died |
| Z5 | 72/f | 0.70 | 1.40 | 0.086 | 24 | 36,000 | hypertension (died) |
| Z6 | 30/f | 3.79 | — | — | / | 29,324 | healthy |
| Z7 | 23/m | 17.2 | — | — | / | 23,156 | healthy |
| | | 36.3 | — | — | / | 22,618 | |

US 8,036,733 B2

DIAGNOSTIC PARAMETER CALCULATION METHOD, SYSTEM FOR DIAGNOSIS AND DIAGNOSTIC PROGRAM

CROSS REFERENCE TO RELATED APPLICATION

This application relates to and claims priority from Japanese Patent Application No. 2004-150375, filed on May 20, 2004 and International Application No. PCT/JP05/009123, filed on May 19, 2005. The entirety of the contents and subject matter of all of the above is incorporated herein by reference.

BACKGROUND OF THE INVENTION

1. Field of the Invention

The present invention relates to a diagnostic parameter calculation method and a system for diagnosis and a diagnostic program, and more particularly, to a diagnostic parameter calculation method, a system for diagnosis and a diagnostic program suitable for diagnosing symptoms of patients through electrocardiogram analysis.

2. Description of the Related Art

Many technologies for diagnosing symptoms of patients by analyzing an electrocardiogram are developed and examples of these technologies include technologies that allow correct diagnosis by accurately and automatically recognizing characteristic points of individual electrocardiogram waveforms (Japanese Patent Laid-Open No. 8-56914, Japanese Patent Laid-Open No. 9-201344, etc.), technologies that make a diagnosis by analyzing individual electrocardiogram waveforms (Japanese Patent Laid-Open No. 10-225443, U.S. Pat. No. 5,609,158, U.S. Pat. No. 5,560,368, etc), and technologies that extract time-series data such as R-R interval from electrocardiogram waveform and make a diagnosis by analyzing the time-series data (U.S. Pat. No. 5,755,671, Japanese Patent Laid-Open No. 6-54815, etc), etc. Using these technologies allows more efficient and more speedy diagnosis than diagnosis depending only on a visual check of electrocardiogram and reduces a possibility of overlooking symptoms.

The above-described conventional technologies carry out an observation and analysis of electrocardiogram waveforms for a few minutes or over 10 minutes at longest, but it is often the case that data suggesting some abnormality of the heart is not obtained in such a short period. For example, if myocardial infarction occurs, there is a danger of sudden death in a few hours due to ventricular tachycardia and the probability that arrhythmia will occur in a few days after the occurrence of myocardial infarction reaches 90%. The rate of occurrence of arrhythmia then reduces, but 5 to 10% of patients die within one year. Therefore it is desirable to acquire and monitor electrocardiogram data for many hours continually for diagnosis of such patients. However, according to the prior arts, a doctor reads the record by the naked eye and makes diagnosis after the recording is finished, or a doctor extracts short time data that he/she regards as abnormal from the recorded data and subjects the data to an automatic analysis, etc. For this reason, there is a large time delay after measurement until the diagnosis result is obtained, and the prior arts are insufficient in prognosticating changes in a symptom or imminent danger. Furthermore, since the prior arts involve judgements through looking electrocardiogram by the naked eye of the doctor, there is a problem that oversight is likely to occur.

BRIEF SUMMARY OF THE INVENTION

It is an object of the present invention to provide a diagnostic parameter calculation method, a system for diagnosis and a diagnostic program which make rapid detection of symptomatical abnormality possible through collection and analysis of long term electrocardiogram data of a patient.

In order to attain the above described object, the present invention provides a diagnostic parameter calculation method for performing diagnosis, comprising the steps of collecting digital electrocardiogram data during a predetermined time interval, detecting R-R intervals of the electrocardiogram data to generate a time-series data, generating a series of partial sets B(j)'s each of which contains n successive elements starting from the j-th element of the time-series data, where n is a constant integer smaller than the total number of elements in the time-series data, calculating a set of characteristic quantities $(y_j, x_j)$ for each partial set B(j), where $y_j$ is the mean value of all elements in the set B(j) and $x_j$ is the mean value of each difference of the first element from each element in the partial set B(j), and calculating a isolation number v and a overlap number u as parameters for diagnosis after splitting (y, x)-plane into lattices, where the isolation number v is the number of the characteristic quantity sets each of which is included in a lattice on (y, x)-plane that does not include any other characteristic quantity set, and the overlap number u is the difference subtracted the isolation number v from the total number of the characteristic quantity sets.

The present invention also provides a diagnostic parameter calculation method for performing diagnosis, comprising the steps of collecting digital electrocardiogram data during a predetermined time interval, detecting R-R intervals of the electrocardiogram data to generate a time-series data, generating a series of partial sets B(j)'s each of which contains n successive elements starting from the j-th element of the time-series data, where n is a constant integer smaller than the total number of elements in the time-series data, calculating a set of characteristic quantities $(y_j, x_j)$ for each partial set B(j), where $y_j$ is the mean value of all elements in the set B(j) and $x_j$ is the mean value of each difference of the first element from each element in the partial set B(j), and calculating a isolation number v, a overlap number u and a maximum overlap degree w as parameters for diagnosis after splitting (y, x)-plane into lattices, where the isolation number v is the number of the characteristic quantity sets each of which is included in a lattice on (y, x)-plane that does not include any other characteristic quantity set, the overlap number u is the difference subtracted the isolation number v from the total number of the characteristic quantity sets, and the maximum overlap degree w is the maximum number of characteristic quantity sets included in a lattice on the (y, x)-plane.

The present invention also provides a diagnostic parameter calculation method for performing diagnosis, comprising the steps of collecting digital electrocardiogram data during a predetermined time interval, detecting R-R intervals of the electrocardiogram data to generate a time-series data, generating a series of partial sets B(j)'s each of which contains n successive elements starting from the j-th element of the time-series data, wherein n is a constant integer smaller than the total number of elements in the time-series data, calculating a set of characteristic quantities $(y_j, x_j)$ for each partial set B(j), wherein $y_j$ is the mean value of all elements in the set B(j) and $x_j$ is the mean value of each difference of the first element from each element in the partial set B(j), and calculating an isolation number v, an overlap number u and a maximum overlap degree w after splitting (y, x)-plane into lattices, wherein the isolation number v is the number of the characteristic quantity sets each of which is included in a lattice on (y, x)-plane that does not include any other characteristic quantity set, the overlap number u is the difference subtracted the isolation number v from the total number of the characteristic quantity sets, and the maximum overlap degree w is the maximum number of characteristic quantity sets included in a lattice on the (y, x)-plane, and calculating a index of heart condition μ as a parameter for diagnosis according to the formula μ=10*v/(u*w), wherein v is the isolation number, u is the overlap number, and w is the maximum overlap degree.

The present invention also provides a diagnostic system including a center equipment and one or more terminal equipments connected to the center equipment via a network, wherein each of the terminal equipment comprises a electrocardiograph, a data collection means for collecting the electrocardiogram data measured by the electrocardiograph and editing the sending data for the center equipment, and a communication interface with the network, and the center equipment comprises a communication interface for receiving the data sent from each the terminal equipment via the network, a recording means for recording the data received with the communication interface, a R-R interval detecting means for detecting R-R intervals of the electrocardiogram data to generate a time-series data, a characteristic quantity calculating means for generating a series of partial sets B(j)'s each of which contains n successive elements starting from the j-th element of the time-series data, where n is a constant integer smaller than the total number of elements in the time-series data, and calculating a set of characteristic quantities $(y_j, x_j)$ for each partial set B(j) where $y_j$ is the mean value of all elements in the set B(j) and $x_j$ is the mean value of each difference of the first element from each element in the partial set B(j), and a diagnostic parameter calculation means for calculating a isolation number v and a overlap number u as parameters for diagnosis after splitting (y, x)-plane into lattices, where the isolation number v is the number of the characteristic quantity sets each of which is included in a lattice on (y, x)-plane that does not include any other characteristic quantity set, and the overlap number u is the difference subtracted the isolation number v from the total number of the characteristic quantity sets.

The present invention also provides a diagnostic system including a center equipment and one or more terminal equipments connected to the center equipment via a network, wherein each of the terminal equipment comprises a electrocardiograph, a data collection means for collecting the electrocardiogram data measured by the electrocardiograph and editing the sending data for the center equipment, and a communication interface with the network, and the center equipment comprises a communication interface for receiving the data sent from each the terminal equipment via the network, a recording means for recording the data received with the communication interface, a R-R interval detecting means for detecting R-R intervals of the electrocardiogram data to generate a time-series data, a characteristic quantity calculating means for generating a series of partial sets B(j)'s each of which contains n successive elements starting from the j-th element of the time-series data, wherein n is a constant integer smaller than the total number of elements in the time-series data, and calculating a set of characteristic quantities $(y_j, x_j)$ for each partial set B(j), wherein $y_j$ is the mean value of all elements in the set B(j) and $x_j$ is the mean value of each difference of the first element from each element in the partial set B(j), and a diagnostic parameter calculation means for calculating an isolation number v, an overlap number u and a maximum overlap degree w as parameters for diagnosis after splitting (y, x)-plane into lattices, wherein the isolation number v is the number of the characteristic quantity sets each of which is included in a lattice on (y, x)-plane that does not include any other characteristic quantity set, the overlap number u is the difference subtracted the isolation number v from the total number of the characteristic quantity sets, and the maximum overlap degree w is the maximum number of characteristic quantity sets included in a lattice on the (y, x)-plane.

The present invention also provides a diagnostic system including a center equipment and one or more terminal equipments connected to the center equipment via a network, wherein each of the terminal equipment comprises a electrocardiograph, a data collection means for collecting the electrocardiogram data measured by the electrocardiograph and editing the sending data for the center equipment, and a communication interface with the network, and the center equipment comprises a communication interface for receiving the data sent from each the terminal equipment via the network, a recording means for recording the data received with the communication interface, a R-R interval detecting means for detecting R-R intervals of the electrocardiogram data to generate a time-series data, a characteristic quantity calculating means for generating a series of partial sets B(j)'s each of which contains n successive elements starting from the j-th element of the time-series data, wherein n is a constant integer smaller than the total number of elements in the time-series data, and calculating a set of characteristic quantities $(y_j, x_j)$ for each partial set B(j), wherein $y_j$ is the mean value of all elements in the set B(j) and $x_j$ is the mean value of each difference of the first element from each element in the partial set B(j), and a diagnostic parameter calculation means for calculating an isolation number v, an overlap number u and a maximum overlap degree w after splitting (y, x)-plane into lattices, wherein the isolation number v is the number of the characteristic quantity sets each of which is included in a lattice on (y, x)-plane that does not include any other characteristic quantity set, the overlap number u is the difference subtracted the isolation number v from the total number of the characteristic quantity sets, and the maximum overlap degree w is the maximum number of characteristic quantity sets included in a lattice on the (y, x)-plane, and calculating a index of heart condition μ as a parameter for diagnosis according to the formula μ=10*v/(u*w), wherein v is the isolation number, u is the overlap number, and w is the maximum overlap degree.

The present invention also provides a diagnostic program for allowing a computer to execute a first step of detecting R-R intervals of the electrocardiogram data collected for a predetermined time interval to generate a time-series data, a second step of generating a series of partial sets B(j)'s each of which contains n successive elements starting from the j-th element of the time-series data, where n is a constant integer smaller than the total number of elements in the time-series data, a third step of calculating a set of characteristic quantities $(y_j, x_j)$ for each partial set B(j), where $y_j$ is the mean value of all elements in the set B(j) and $x_j$ is the mean value of each difference of the first element from each element in the partial set B(j), and a fourth step of calculating a isolation number v and a overlap number u as parameters for diagnosis after splitting (y, x)-plane into lattices, where the isolation number v is the number of the characteristic quantity sets each of which is included in a lattice on (y, x)-plane that does not include any other characteristic quantity set, and the overlap number u is the difference subtracted the isolation number v from the total number of the characteristic quantity sets.

The present invention also provides a diagnostic program for allowing a computer to execute a first step of detecting R-R intervals of the electrocardiogram data collected for a predetermined time interval to generate a time-series data, a second step of generating a series of partial sets B(j)'s each of which contains n successive elements starting from the j-th element of the time-series data, where n is a constant integer smaller than the total number of elements in the time-series data, a third step of calculating a set of characteristic quantities $(y_j, x_j)$ for each partial set B(j), where $y_j$ is the mean value of all elements in the set B(j) and $x_j$ is the mean value of each difference of the first element from each element in the partial set B(j), and a fourth step of calculating a isolation number v, a overlap number u and a maximum overlap degree w as parameters for diagnosis after splitting (y, x)-plane into lattices, where the isolation number v is the number of the characteristic quantity sets each of which is included in a lattice on (y, x)-plane that does not include any other characteristic quantity set, the overlap number u is the difference subtracted the isolation number v from the total number of the characteristic quantity sets, and the maximum overlap degree w is the maximum number of characteristic quantity sets included in a lattice on the (y, x)-plane.

The present invention also provides a diagnostic program for allowing a computer to execute a first step of detecting R-R intervals of the electrocardiogram data collected for a predetermined time interval to generate a time-series data, a second step of generating a series of partial sets B(j)'s each of which contains n successive elements starting from the j-th element of the time-series data, wherein n is a constant integer smaller than the total number of elements in the time-series data, a third step of calculating a set of characteristic quantities $(y_j, x_j)$ for each partial set B (j), wherein $y_j$ is the mean value of all elements in the set B (j) and $x_j$ is the mean value of each difference of the first element from each element in the partial set B (j), a fourth step of calculating an isolation number v, an overlap number u and a maximum overlap degree w after splitting (y, x)-plane into lattices, wherein the isolation number v is the number of the characteristic quantity sets each of which is included in a lattice on (y, x)-plane that does not include any other characteristic quantity set, the overlap number u is the difference subtracted the isolation number v from the total number of the characteristic quantity sets, and the maximum overlap degree w is the maximum number of characteristic quantity sets included in a lattice on the (y, x)-plane, and a fifth step of calculating a index of heart condition μ as a parameter for diagnosis according to the formula μ=10*v/(u*w), wherein v is the isolation number, u is the overlap number, and w is the maximum overlap degree.

DETAILED DESCRIPTION OF THE PREFERRED EMBODIMENTS

Embodiments of the present invention will be explained in detail below. R-R intervals known as a typical characteristic quantity of electrocardiogram, and successive R-R intervals of a electrocardiogram constitutes a time series data that has one value per one heart beat. This time-series data of R-R intervals generally has different feature from one person to another. For example, when the R-R intervals of plural healthy persons who stay equally tranquil are measured, the average R-R interval may vary from one person to another, such as 1 second for a person (heart beat per minute of 60) while 6/7 second for another person (heart beat per minute of 70). Moreover, the R-R interval of a person is not completely constant but varying minutely. Furthermore, after taking exercise or when symptom changes, the average value of R-R interval as well as minute variation may change. The present invention is intended to make a diagnosis by analyzing such time-series data.

Figure 1:
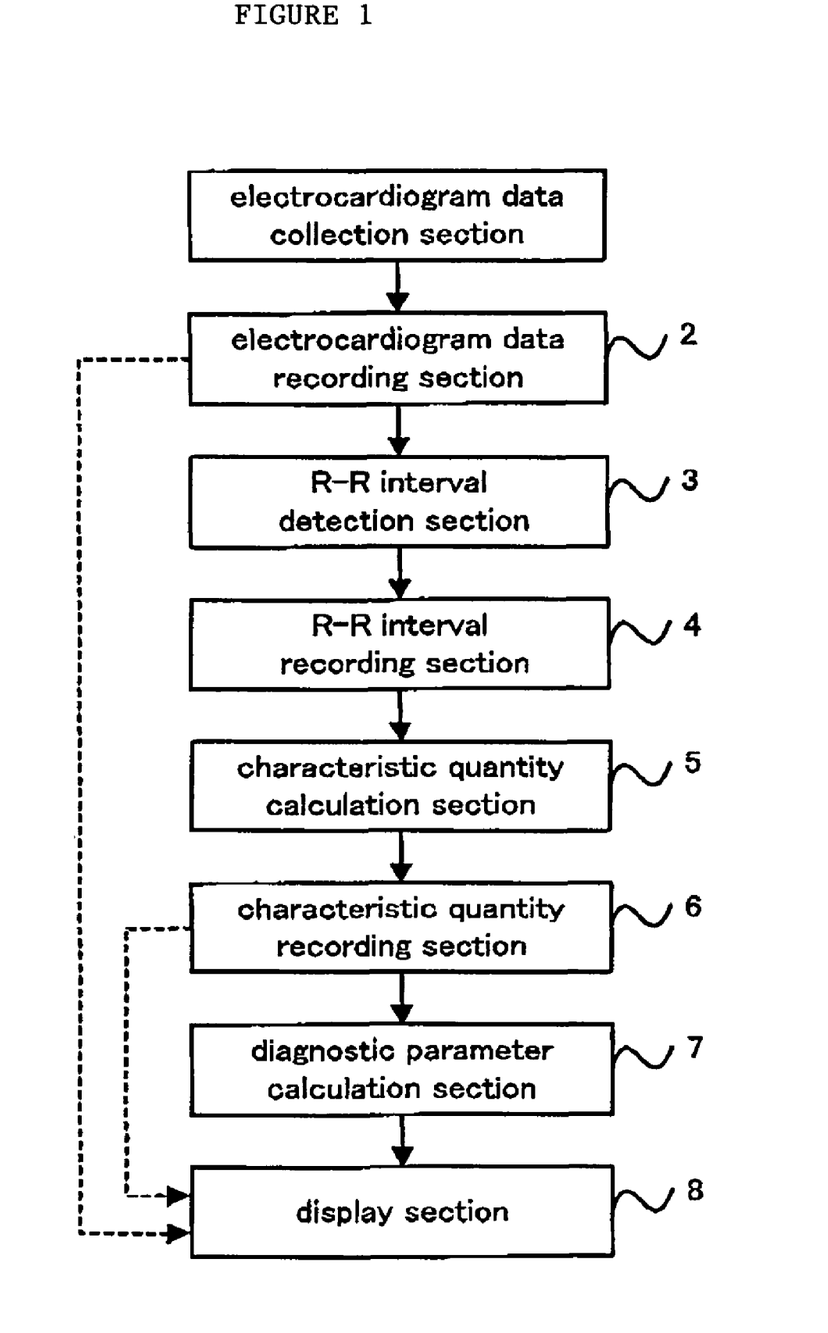
FIG. 1 is a block diagram showing functional configuration of a diagnostic system according to the present invention.

FIG. 1 is a functional block diagram showing a diagnostic system according to the present invention. In the electrocardiogram data collection section 1 in FIG. 1, the electrocardiogram data measured for a long time interval such as 5 hours with a electrocardiograph are digitized and are recorded in the electrocardiogram data recording section 2 in FIG. 1. Assuming 1 millisecond sampling rate and 12 bits cording for each sampling data in the above digitization, the number of sampled data is 1000/sec and 3.6×10⁶/hour, which corresponds to information rate of 1.5 KB (kilobytes)/sec or 5.4 MB (megabytes)/hour.

In the R-R interval detection section 3 in FIG. 1, R-points $\{R_j, j=0, 1, 2 \ldots \}$, the times at which each R-wave on the electrocardiogram takes its peak value, are first detected by analyzing the electrocardiogram data recorded in the electrocardiogram recording section 2. Then a time-series data $\{r_j, j=0, 1, 2 \ldots \}$ is calculated according to formula (1) in the section 3.

$$r_j = |R_{j+1} - R_j|, 0 \leq j \leq N-1 \qquad \text{[Formula 1]}$$

where N+1 is the number of detected R-points, $R_j$ (j=0~N) is the jth R-point ordered in time, and $r_j$ is R-R interval of adjacent R-points. The calculated time-series data $\{r_j; j=0~N\}$ is recorded in R-R interval recording section 4 in FIG. 1. If the number of heart beat is 70/minute for a person, the number of R-R intervals will be 4,200/hour because time-series data $\{r_j\}$ has one value per one heart beat. This means 4,200×1.5 bytes=6.3 KB data per an hour will be generated when each R-R interval $r_j$ is 12 bits data.

In the characteristic quantity calculation section 5 in FIG. 1, M+1 partial sets B(j)'s of the whole set constituting of all elements in the time-series data recorded in the section 4 are composed first as formula (2), $$B(j) = (r_j, r_{j+1}, \ldots r_{j+n}), 0 \leq j \leq M, \qquad \text{[Formula 2]}$$

where n is a integer smaller than N in formula (1), and M is a integer given by $$M=N-n-1 \quad \text{[Formula 3]}$$

Then, the quantities $y_j$ and $x_j$ for each set B(j), j=0~M, where $y_j$ is the mean value of n+1 elements in the set B(j) and $x_j$ is the mean value of n differences of each element from the first element $r_j$ in the set B(j), are calculated as the characteristic quantity of the measured electrocardiogram data according to formula (4) and (5);

$$y_j = \sum_{k=0}^{n} r_{j+k}/(n+1), 0 \leq j \leq M \quad \text{[Formula 4]}$$

$$x_j = \sum_{k=1}^{n} (r_{j+k} - r_j)/n = (n+1)(y_j - r_j)/n, \quad \text{[Formula 5]}$$
$$0 \leq j \leq M$$

formula (5) shows that only several calculations are needed for the characteristic quantities $x_j$'s if $y_j$ is given for each j. Moreover calculations of the characteristic quantities $y_j$'s are made efficient by applying a recurrence formula as follows. When M+1 quantities $P_j$, j=0~M are defined by formula (6);

$$P_j=(n+1)y_j, 0 \leq 1 \leq M \quad \text{[Formula 6]}$$

next recursive formula is derived easily from formula (4) and (6) as follows;

$$P_0 = \sum_{k=0}^{n} r_k, P_{j+1} = P_j + r_{j+n+1} - r_j, 0 \leq 1 \leq M \quad \text{[Formula 7]}$$

Therefore each calculation of $P_{j+1}$, $0 \leq j \leq M-1$ can be successively executed by one addition operation and one subtraction operation after the value $P_0$ is calculated by n addition operations. The characteristic quantities $y_j$'s are given by dividing $P_j$ by the constant n+1. Calculated characteristic quantities $y_j$'s and $x_j$'s are recorded in the characteristic quantity recording section 6 in FIG. 1.

In the diagnostic parameter calculation section 7 in FIG. 1, three parameters denoted as u, v and w are derived, which shows the state of distribution of characteristic quantity sets ($y_j$, $x_j$), j=0~M on (y, x)-plane, where $y_j$ and $x_j$, j=0~M are those recorded in the recording section 6. First, (y, x)-plane is divided into rectangular lattices each of which has four sides of q millisecond length and parallel to y or x axis, and each characteristic quantity set ($y_j$, $x_j$) is plotted on the (y, x)-plane. Then, some lattice on the plane will include only one characteristic quantity set, and some other lattice will include plural characteristic quantity sets. Next, the isolation number v, the number of characteristic quantity set included in a lattice which does not include any other characteristic quantity set, is counted. Then the overlap number u is calculated now by subtracting the isolation number v from M+1, the total number of characteristic quantity sets recorded in the recording section 6;

$$u=M-v+1 \quad \text{[Formula 8]}$$

This overlap number u is equal to the number of characteristic quantity sets each of which is included in a lattice including at least one other characteristic quantity set.

Furthermore, maximum overlap degree w is defined as shown bellow. The overlap degree of lattice is defined for each lattice on (y, x)-plane as the number of characteristic quantity sets included in the lattice. This overlap degree of lattice has the value larger than 0 and less than M+1, therefore they must have its maximum value, and this maximum value of overlap degree of lattice over all lattices is defined as maximum overlap degree w.

These parameters calculated from the electrocardiogram of a person will show the heart condition of the person because the larger the overlap number u in comparison with the isolation number v and the larger the maximum overlap degree w are, the smaller the time variation of R-R interval is, and very small time variation of R-R interval is considered to mean that the response of the heart to various stimulus is dull. This fact allows diagnosis by utilizing these three parameters derived automatically from the electrocardiogram measured for a long time interval. Moreover, direct observation or analysis of these three parameters may make diagnosis complicated. Therefore, in this invention, an index of heart condition µ is defined by formula (9) as other parameter for diagnosis.

$$\mu=10*v/(u*w), \quad \text{[Formula 9]}$$

where the coefficient 10 is multiplied for the index µ to have the value easy to comprehend, though it may be another value.

It is easily verified from formulas (8) and (9) that the index µ becomes smaller as the overlap number u becomes larger in comparison with the isolation number v and the maximum overlap degree w becomes larger, so that the lower value of the index of heart condition µ means duller response of the heart to various stimulus as mentioned above. Therefore, the index µ can be considered to be a useful parameter for diagnosis.

In the display section 8 in FIG. 1, the index of heart condition µ calculated in the diagnostic parameter calculation section 7 is indicated to serve for diagnosis, and the electrocardiogram data stored in the electrocardiogram data recording section 2 can be indicated for the doctors who requires it to observe on a display. Moreover, it is useful to indicate on the display section 8 the representative point of each square lattice with color corresponding to the overlap degree of the lattice, where representative point is, for example, the center point of the lattice. This indication means the distribution of the characteristic quantity sets on the (y, x)-plane, and shows the heart condition visually because it is observed through experiments that the smaller is the index of heart condition µ, the narrower is the range in which many of representative points with colors corresponding to the overlap degree larger than 2 are included.

Figure 7:
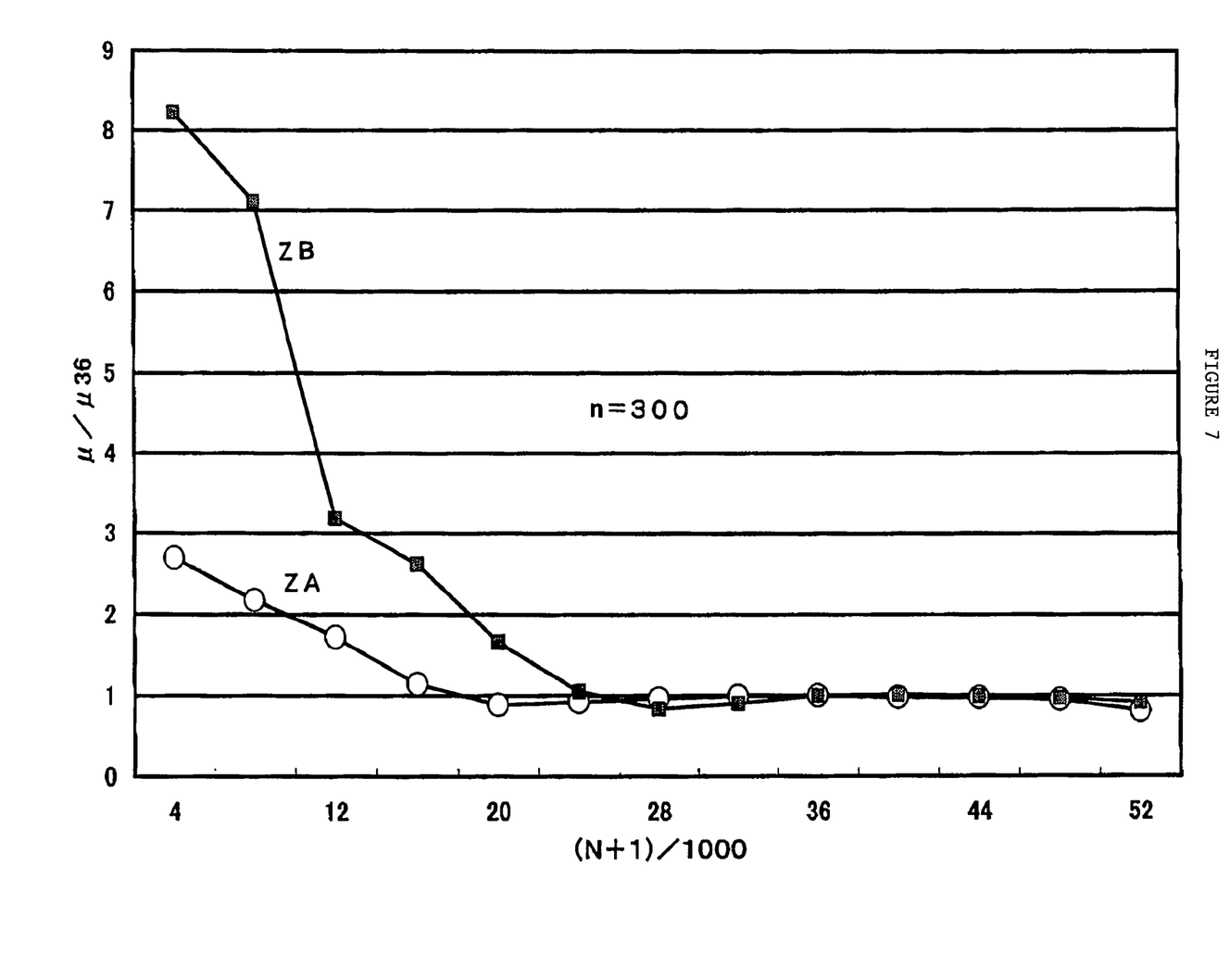
FIG. 7 is a chart showing variation of measured and resultant μ values for various data collection intervals.

Several experimental results about the index of heart condition µ are shown below. FIG. 7 shows the variations of the index of heart condition µ derived from measured electrocardiogram data collected from two subjects ZA and ZB for various time duration. In these examples, the digitization of electrocardiogram data has been performed by 1 millisecond sampling and 12 bits quantization, n, the number of elements of partial sets B(j)'s, was 300, and each rectangular lattice on (y, x)-plane was 1 millisecond square. Horizontal axis and vertical axis in FIG. 7 are graduated in (N+1)/1000 wherein N+1 is the number of R-points used for diagnosis analysis, and the normalized index of heart condition µ/$\mu_{36}$ wherein $\mu_{36}$ is the value of the index of heart condition for (N+1)/1000=36, respectively. (N+1)/1000=36 in the horizontal axis corresponds to electrocardiogram data during 10 hours when cardiac beat rate is 60 per minute, and if the cardiac beat rate is different from 60 per minute, the same value of (N+1)/1000=36 in horizontal axis corresponds to electrocardiogram data during time interval different from 10 hours.

The resultant curves in FIG. 7 show that the indexes of heart condition of the subjects ZA and ZB take almost constant value for N larger than about 20,000, and this situation was verified for another subjects. Therefore, if the data including R-points larger than about 20,000 is collected in electrocardiogram data collection section 1, the data may be enough to make a diagnosis when the size of partial set is 300.

Figure 8:
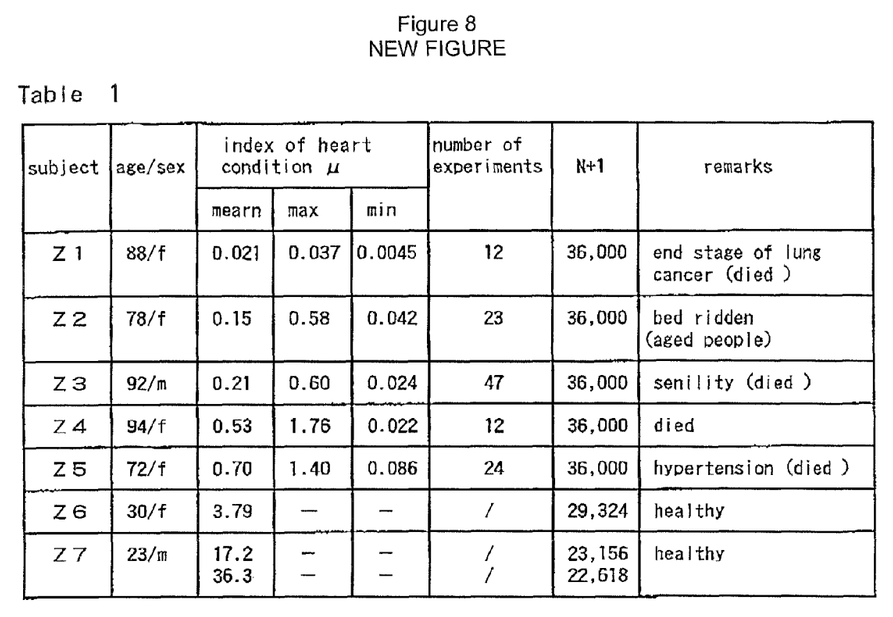
FIG. 8 is a table showing experimental results about seven different subjects, including remarks.

FIG. 8 shows the experimental results about 7 subjects with some remarks on them. In this experiment, the digitization parameters and the size of partial set n are equal to those in FIG. 7. In FIG. 8, the number of experiments per subject="12" and the number of included R-point="*36,000" for the subject Z1 mean that the number of included R-points was 36,000 for all 12 times of experiments, and only the mean, maximum, and minimum value of the index of heart condition resulted from 12 times of experiments are shown. It's the same for other subjects Z2-Z5. For the subject Z6, an experiment collecting electrocardiogram data including 29,324 R-points was performed, resulting in an index of heart condition p of 3.79. For the subject Z7, two experiments collecting electrocardiogram data including 23,156 and 22,618 R-points were performed, resulting in the index of heart condition $\mu$ of 17.2 and 36.3 respectively. The notation "died" in the remarks column in FIG. 8 means that the corresponding subject died several weeks after the last experiment.

The results for subjects Z1-Z5 in FIG. 8 show that the index of heart condition $\mu$ can take fairly wide range of values when many times of experiments for a subject are performed. It seems that such variation of the index of heart condition $\mu$ of a subject is representing his heart condition when each experiment is performed. But taking a large view of things, the index of heart condition $\mu$ of about 1 or smaller is considered to be indicating corresponding subject is not healthy or in dangerous heart condition, such as the subjects Z1-Z5 in FIG. 8, while the index of heart condition $\mu$ of fully larger than 1 is considered to be indicating the corresponding subject is healthy such as the subjects Z6 and Z7 in FIG. 8. Such relation of the index of heart condition $\mu$ with the health condition of corresponding subject is verified for subjects other than those listed in FIG. 8, though the results for them are abbreviated in FIG. 8. Therefore the index of heart condition $\mu$ calculated automatically from one's electrocardiogram dais can be regarded as a efficient index for diagnosis on his heart condition, and is used as the index for diagnosis in this invention.

According to the diagnostic system illustrated in FIG. 1, unusual state of heart condition may be discovered through automatic derivation of parameters u, v, and w from the electrocardiogram of a person for a long time interval such as several hours, instead of a shorter time interval, and it is attained that a doctor can recommend preventive measures against diseases for not only patients who are considered already have cardiac disease but also people who are considered to be healthy. Moreover, though occasional detection errors of R-points may happen, such errors will have little effect on the diagnosis because the diagnostic parameters are derived through statistical processing.

Next, an example of actual diagnostic system configuration in this invention will be described below. Generally the place and time in which electrocardiogram data of a person is collected is not necessarily the same place and time in which the electrocardiogram data is observed and analyzed. Moreover, a set of apparatus for R-R interval detection section, characteristic quantities calculation section, and diagnostic parameter calculation section etc in FIG. 1 can be used effectively for analysis of electrocardiogram data collected from plural persons.

Figure 2:
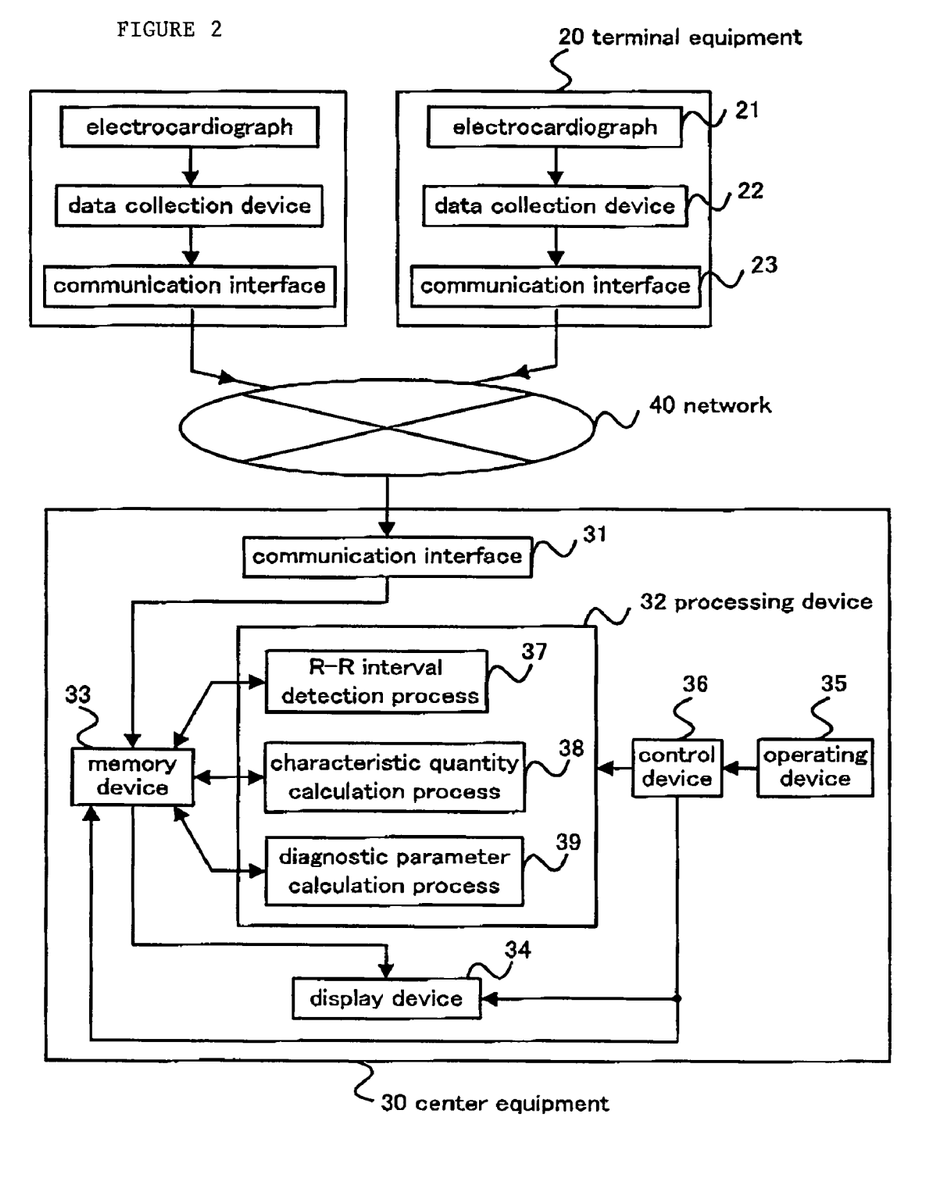
FIG. 2 is a block diagram showing a configuration example of diagnostic system according to the present invention.

These considerations mentioned above lead to, for example, a diagnostic system shown in FIG. 2, where each terminal equipment 20 is connected with a center system 30 via a network 40. In the terminal equipments, the data collection device 22 collects electrocardiogram data measured by the electrocardiograph 21, and produces sending data. The communication interface 23 send it out to the network 40. It is possible for the data collection device 22 to collect the electrocardiogram data measured by plural electrocardiographs and produce their sending data when plural electrocardiographs are included in the terminal equipment.

The electrocardiogram data collected by the electrocardiograph should be digitized in early stage as soon as possible, so as to make effective processing, recording, and transmitting the data. Therefore the digitization should be done at output stage of the electrocardiograph 21 or input stage of the data collection device 22. If the electrocardiogram data are digitized with 1 millisecond sampling and 12 bits coding, the rate of generated digital data will be 12 kilo-bits/second=1.5 KB/second, which can be send effectively to the center system 30 in burst mode via the network 40 such as Internet, Ethernet or mobile communication network.

In the center system 30 in FIG. 2, the electrocardiogram data sent from each terminal equipment via network 40 are received at the communication interface 31 and recorded on the memory device 33, where the communication interface such as a network server can instantaneously receive the data from many terminal equipments. In the processing device 32, R-R intervals of the received electrocardiogram data, the characteristic quantities and the diagnostic parameters are calculated, and these are displayed on the display device 34. The control device 36 controls the operation of the processing device 32 and the display device 34 according to the commands given by the operating device 35.

In the processing device 32, R-R interval detection process 37, characteristic quantity calculation process 38, and diagnostic parameter calculation process 39 are provided with, corresponding respectively to the R-R interval detection section 3, the characteristic quantities calculation section 5, and diagnostic parameter calculation section 7 in FIG. 1.

In the R-R interval detection process 37, an electrocardiogram data on the memory device 33 is read in after the instruction given by the operating device 35, R-R intervals are detected from the data, and the resultant R-R intervals are recorded on the memory device 33. Well-known method of R-R interval detection can be used, and the detail description of the method is abbreviated here.

Figure 3:
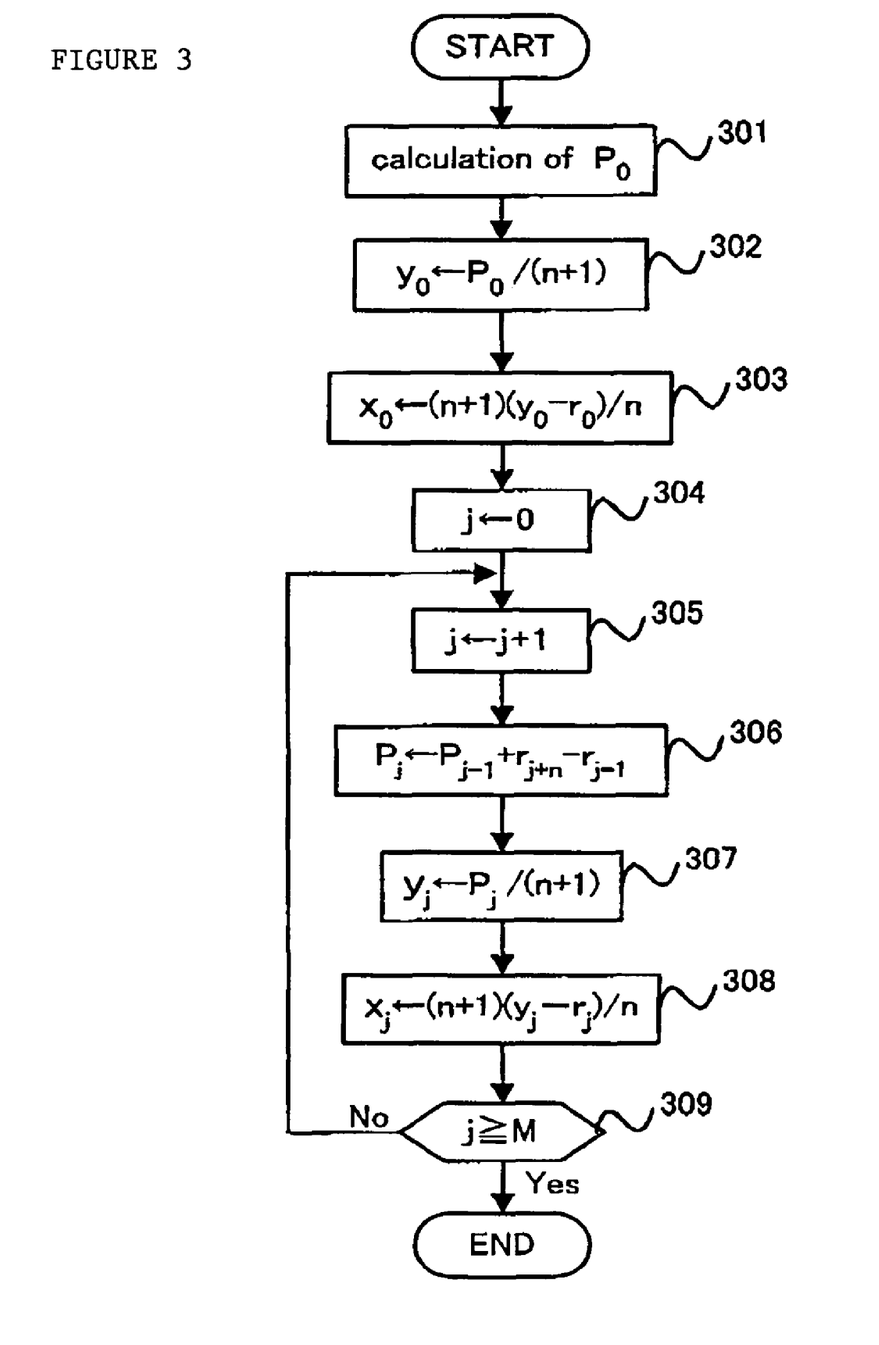
FIG. 3 is a flow chart showing a characteristic quantity calculation algorithm.

In the characteristic quantity calculation process 38, a R-R interval data of a person detected in the R-R interval process 37 is read in, and is processed according to the flow chart shown in FIG. 3 which is an example of algorithm for characteristic quantity calculation. In this figure, the steps from 301 to 303 calculate the quantities $P_0$, $y_0$, $x_0$ according to formulas (7), (5), and (4) respectively for j=0. Then the steps from 304 to 309 calculate the quantities $P_j$, $y_j$, and $x_j$ according to formulas (7), (5), and (4) respectively for j=1~M. The resultant characteristic quantities $(y_j, x_j)$, j=0~M are recorded on the memory device 33.

Figure 4:
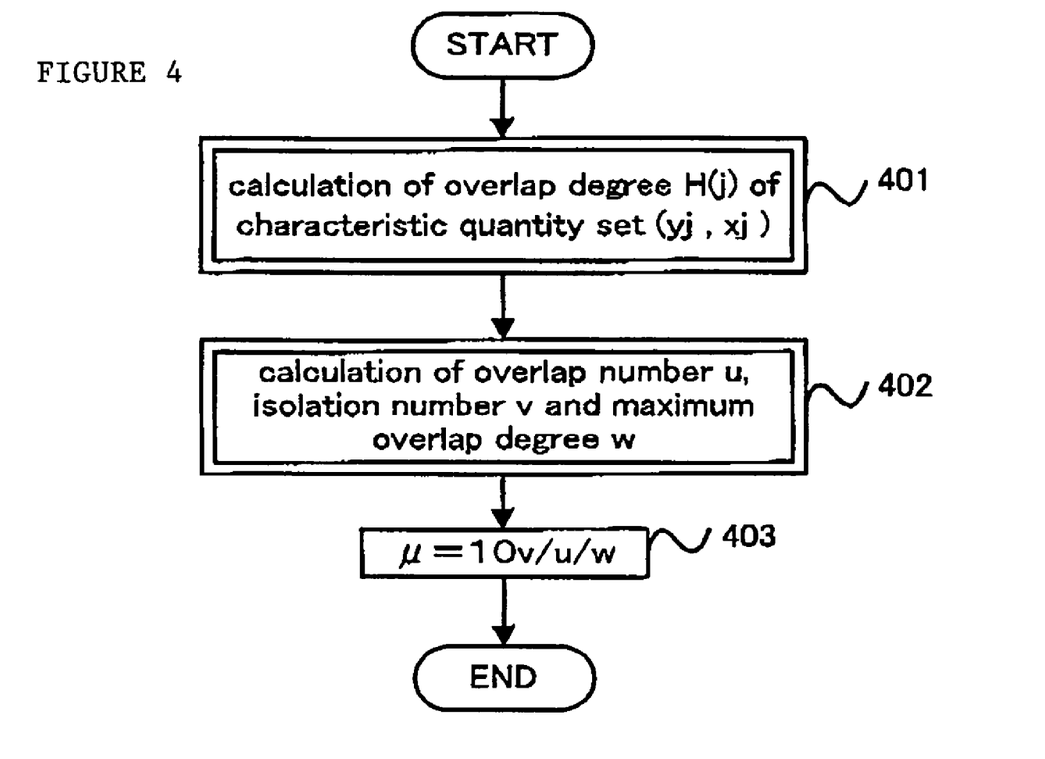
FIG. 4 is a flow chart showing a general algorithm for diagnostic parameter calculation process.

In the diagnostic parameter calculation process 39, all characteristic quantity data for a person calculated in the process 38 is read in, and are processed according to the flow chart shown in FIG. 4, which is an example of algorithm for the diagnostic parameter calculation. In this algorithm, the overlap degree H(j) of each characteristic quantity set $(y_j, x_j)$ is calculated in step 401, where the overlap degree H(j) is the number of characteristic quantity set included in the lattice which includes the characteristic quantity set $(y_j, x_j)$, and is equal to the overlap degree of the lattice which includes the characteristic quantity set $(y_j, x_j)$. For example, if a lattice on (y, x)-plane includes just three characteristic quantity sets $(y_1,$ $x_1$), ($y_5$, $x_5$), and ($y_6$, $x_6$), the overlap degrees of these characteristic quantity sets H(1), H(5), and H(6), and the overlap degree of the lattice are all equal to 3. It is easily verified that the overlap degree of characteristic quantity set H(j) has always the value larger than 1, the number of characteristic quantity set having the overlap degree of 1 is equal to the isolation number v, the number of characteristic quantity set having the overlap degree larger than 2 is equal to the overlap number u, and the maximum value of H(j) is equal to the maximum overlap degree w previously defined.

Next the overlap number u, isolation number v, and maximum overlap degree w are calculated in step 402, and the index of heart condition μ is calculated in step 403 and is recorded on the memory device 33 with the parameters u, v and w. The resultant index of heart condition and the three parameters may be displayed on the display device 34. Details of the processes in step 401 and 402 will be described bellow.

Figure 5:
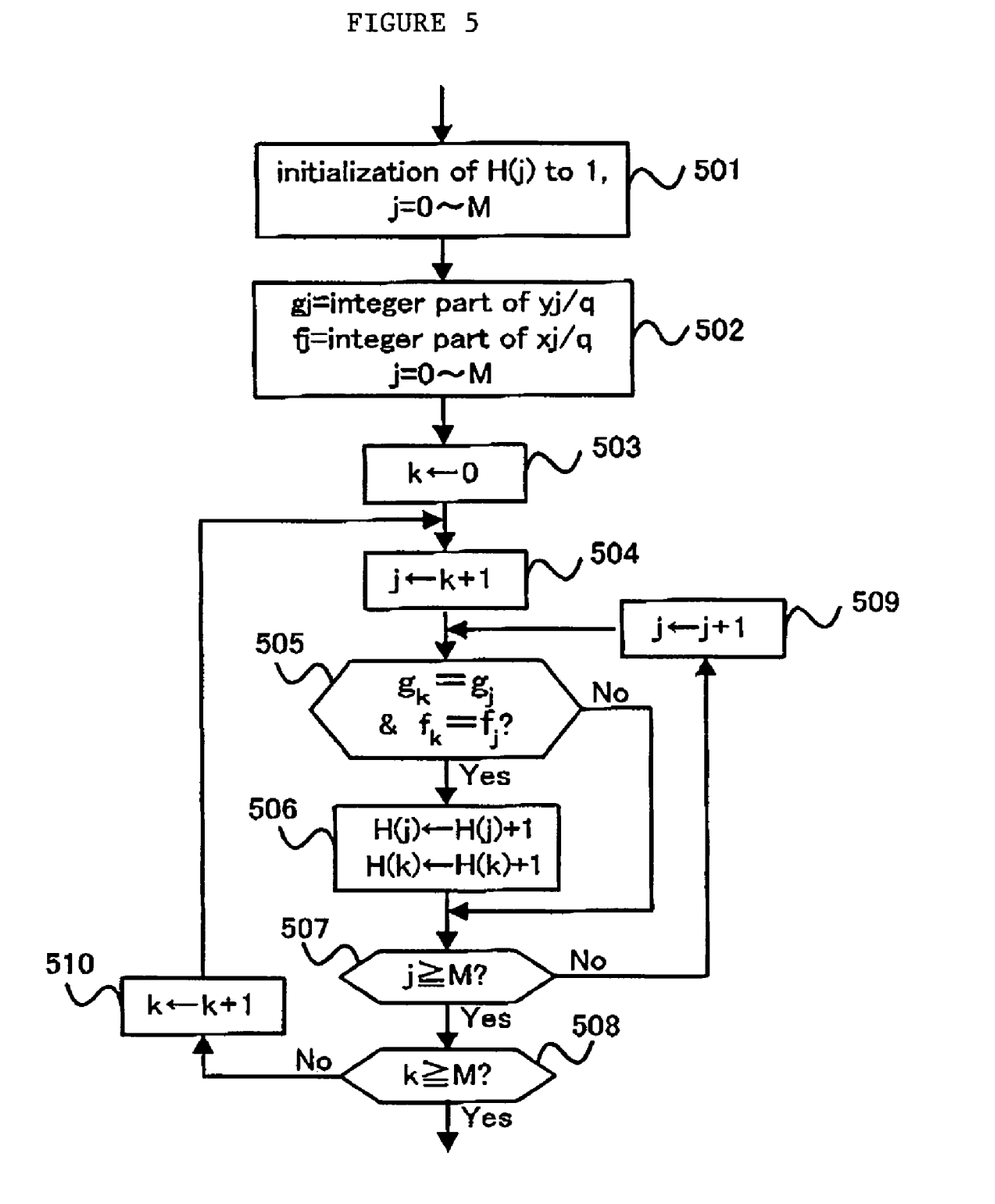
FIG. 5 is a flow chart showing details of the step 401 in FIG. 4.

The flow chart shown in FIG. 5 illustrates the details of the process of step 401 in FIG. 4. When (y, x)-plane is divided into rectangular lattices by linear lines y=0, y=±q, y=±2q ... and x=0, x=±q, x=±2q ..., the range of each lattice is given by formula (10);

$$g*q \leq y < (g+1)*q,$$

$$f*q \leq x < (f+1)*q,$$  [Formula 10]

where g and f are integers, and the lattice with the range specified by formula (10) for a set of integers (g, f) can be called as (g, f)-lattice.

Now in FIG. 5, all overlap degree H(j)'s are first initialized to 1 in step 501, and a set of integer ($g_j$, $f_j$) for each characteristic quantity set ($y_j$, $x_j$), j=0~M is calculated using formula (11) in step 502;

$$g_j = \text{integer part of } y_j/q, f_j = \text{integer part of } x_j/q$$  [Formula 11]

Using this set of integer ($g_j$, $f_j$), it can be said that the characteristic quantity set ($y_j$, $x_j$) is included in the ($g_j$, $f_j$)-lattice.

In steps from 503 to 510, the overlap degree H(j) of each characteristic quantity set ($y_j$, $x_j$, 0≤j≤M) is calculated, where it is utilized that two characteristic quantity sets ($y_j$, $x_j$) and ($y_k$, $x_k$) for j≠k should be included in a same lattice if and only if the condition $g_j=g_k$ and $f_j=f_k$ are valid as shown in step 505.

Figure 6:
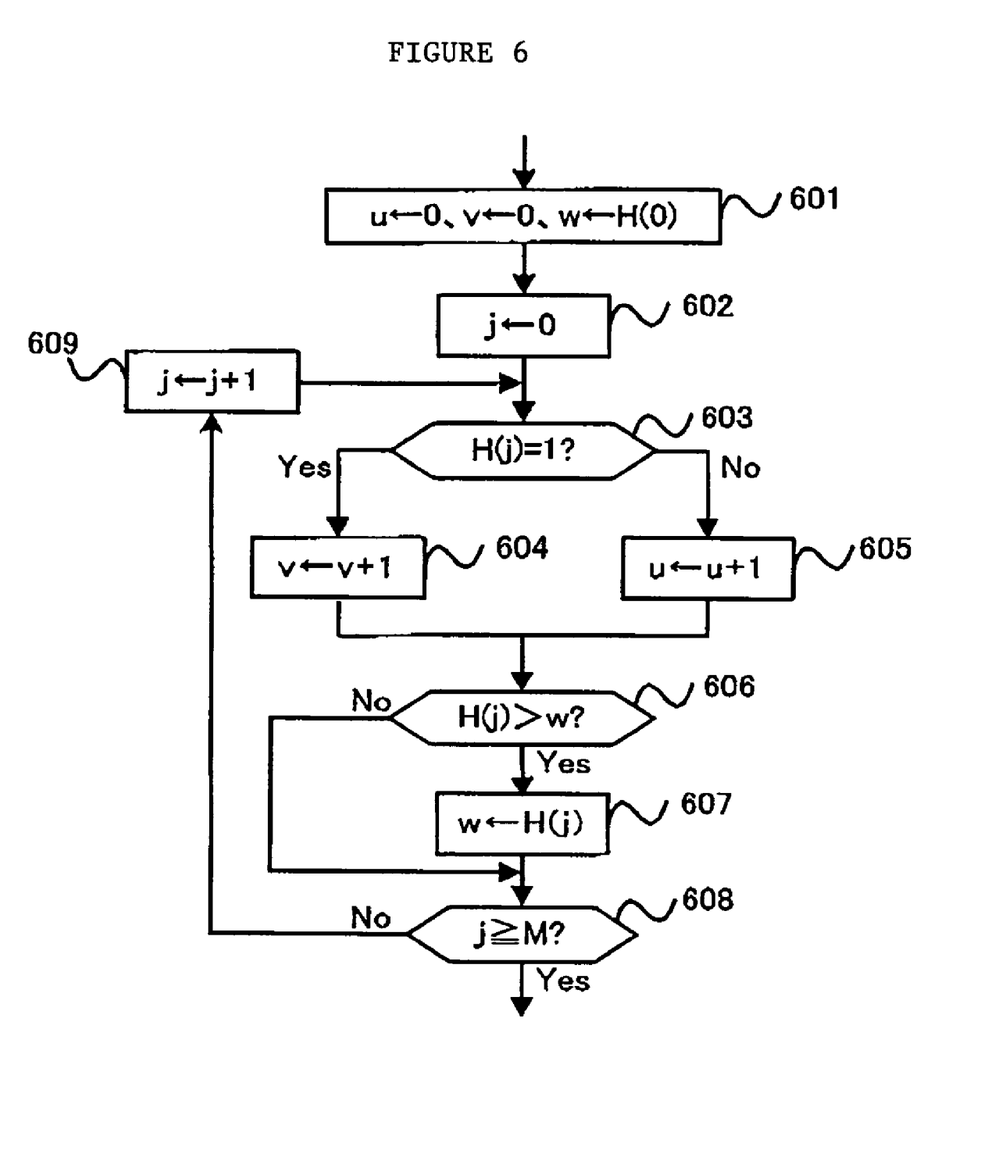
FIG. 6 is a flow chart showing details of the step 402 in FIG. 4.

The flow chart in FIG. 6 illustrates the details of step 402 in FIG. 5. After the initialization where both of the overlap number u and the isolation number v are set to 0, and maximum overlap degree w of characteristic quantity set is set to H(0) in step 601, the overlap number u and the isolation number v are counted up in step 603~605, and the maximum overlap degree w is refined by checking the value of the overlap degree H(j) in steps 606 and 607 varying j from 0 to M in steps 602, 608 and 609.

On the display device 34 in FIG. 2, not only the three parameters u, v, w and the index of heart condition μ calculated in the diagnostic parameter calculation process 39, but also the electrocardiogram itself transmitted from the terminal equipment or the distribution of the characteristic quantity distribution on the (y, x)-plane which is reflecting the heart condition as mentioned before can be displayed according to the instruction from the operating device 35.

The invention claimed is:

1. A computer-implemented diagnostic parameter calculation method for performing diagnosis, comprising the steps of:

collecting digital electrocardiogram data during a predetermined time interval;

detecting R-R intervals of the electrocardiogram data to generate a time-series data;

generating a series of partial sets B(j)'s, each of which contains n successive elements starting from the j-th element of said time-series data, wherein n is a constant integer smaller than the total number of elements in said time-series data;

calculating, using a computer, a set of characteristic quantities ($y_j$, $x_j$) for each partial set B(j) wherein $y_j$ is the mean value of all elements in the set B(j) and $x_j$ is the mean value of each difference of the first element from each element in the partial set B(j); and calculating, using a computer, an isolation number v and an overlap number u as parameters for diagnosis after splitting (y, x)-plane into lattices, wherein said isolation number v is the number of said characteristic quantity sets each of which is included in a lattice on (y, x)-plane that does not include any other characteristic quantity set, and said overlap number u is the difference subtracted said isolation number v from the total number of said characteristic quantity sets;

wherein calculated isolation number v and overlap number u are used as parameters for diagnosis of a condition of a heart of a patient.

2. A computer-implemented diagnostic parameter calculation method for performing diagnosis, comprising the steps of:

collecting digital electrocardiogram data during a predetermined time interval;

detecting R-R intervals of the electrocardiogram data to generate a time-series data;

generating a series of partial sets B(j)'s, each of which contains n successive elements starting from the j-th element of said time-series data, wherein n is a constant integer smaller than the total number of elements in said time-series data;

calculating, using a computer, a set of characteristic quantities ($y_j$, $x_j$) for each partial set B(j) wherein $y_i$ is the mean value of all elements in the set B(j) and $x_i$ is the mean value of each difference of the first element from each element in the partial set B(j); and calculating, using a computer, an isolation number v, an overlap number u and a maximum overlap degree w as parameters for diagnosis after splitting (y, x)-plane into lattices, wherein said isolation number v is the number of said characteristic quantity sets each of which is included in a lattice on (y, x)-plane that does not include any other characteristic quantity set, said overlap number u is the difference subtracted said isolation number v from the total number of said characteristic quantity sets, and said maximum overlap degree w is the maximum number of characteristic quantity sets included in a lattice on said (y, x)-plane;

wherein calculated isolation number v, overlap number u and maximum overlap degree w are used as parameters for diagnosis of a condition of a heart of a patient.

3. A computer-implemented diagnostic parameter calculation method for performing diagnosis, comprising the steps of:

collecting digital electrocardiogram data during a predetermined time interval;

detecting R-R intervals of the electrocardiogram data to generate a time-series data;

generating a series of partial sets B(j)'s, each of which contains n successive elements starting from the j-th element of said time-series data, wherein n is a constant integer smaller than the total number of elements in said time-series data;

calculating, using a computer, a set of characteristic quantities $(y_j, x_j)$ for each partial set B(j) wherein $y_j$ is the mean value of all elements in the set B(j) and $x_j$ is the mean value of each difference of the first element from each element in the partial set B(j); and calculating, using a computer, an isolation number v, an overlap number u and a maximum overlap degree w after splitting (y, x)-plane into lattices, wherein said isolation number v is the number of said characteristic quantity sets each of which is included in a lattice on (y, x)-plane that does not include any other characteristic quantity set, said overlap number u is the difference subtracted said isolation number v from the total number of said characteristic quantity sets, and said maximum overlap degree w is the maximum number of characteristic quantity sets included in a lattice on said (y, x)-plane; and calculating, using a computer, a index of heart condition μ as a parameter for diagnosis according to the formula μ=10*v/(u*w), wherein v is said isolation number, u is said overlap number, and w is said maximum overlap degree;

wherein said index of heart condition is used to diagnose a condition of a heart of a patient.

4. A diagnostic system, comprising:
a network;
one or more terminal equipment connected to said network, each of said one or more terminal equipment including:
  a electrocardiograph;
  a data collection means for collecting electrocardiogram data measured by said electrocardiograph and editing collected electrocardiogram data into a format appropriate for sending; and
  a communication interface configured to send data via said network; and
a center equipment connected to said one or more terminal equipment via said network, said center equipment including:
  a communication interface configured to receive the data sent from each of said one or more terminal equipment via said network;
  a recording means for recording the data received with said communication interface;
  a R-R interval detecting means for detecting R-R intervals of the electrocardiogram data to generate a time-series data;
  a characteristic quantity calculating means for generating a series of partial sets B(j)'s, each of which contains n successive elements starting from the j-th element of said time-series data, wherein n is a constant integer smaller than the total number of elements in said time-series data, and for calculating a set of characteristic quantities $(y_j, x_j)$ for each partial set B(j) wherein $y_j$ is the mean value of all elements in the set B(j) and $x_j$ is the mean value of each difference of the first element from each element in the partial set B(j); and
  a diagnostic parameter calculation means for calculating an isolation number v and an overlap number u as parameters for diagnosis after splitting (y, x)-plane into lattices, wherein said isolation number v is the number of said characteristic quantity sets each of which is included in a lattice on (y, x)-plane that does not include any other characteristic quantity set, and said overlap number u is the difference subtracted said isolation number v from the total number of said characteristic quantity sets;

wherein calculated isolation number v and overlap number u are used as parameters for diagnosis of a condition of a heart of a patient.

5. The diagnostic system of claim 4,
wherein said diagnostic parameter calculation means are further adapted for calculating a maximum overlap degree w as a parameter for diagnosis after splitting (y, x)-plane into lattices; and wherein said maximum overlap degree w is the maximum number of characteristic quantity sets included in a lattice on said (y, x)-plane; and wherein calculated isolation number v, overlap number u and maximum overlap degree w are used as parameters for diagnosis of a condition of a heart of a patient.

6. The diagnostic system of claim 5,
wherein said diagnostic parameter calculation means are further adapted for calculating a index of heart condition μ as a parameter for diagnosis according to the formula μ=10*v/(u*w), wherein v is said isolation number, u is said overlap number, and w is said maximum overlap degree; and wherein said index of heart condition is used to diagnose a condition of a heart of a patient.

7. A computer-implemented diagnostic program, comprising:
a first step of detecting R-R intervals of electrocardiogram data collected for a predetermined time interval to generate a time-series data;
a second step of generating a series of partial sets B(j)'s, each of which contains n successive elements starting from the j-th element of said time-series data, wherein n is a constant integer smaller than the total number of elements in said time-series data;
a third step of calculating, using a computer, a set of characteristic quantities $(y_j, x_j)$ for each partial set B(j) wherein $y_j$ is the mean value of all elements in the set B(j) and $x_j$ is the mean value of each difference of the first element from each element in the partial set B(j); and
a fourth step of calculating, using a computer, an isolation number v and an overlap number u as parameters for diagnosis after splitting (y, x)-plane into lattices, wherein said isolation number v is the number of said characteristic quantity sets each of which is included in a lattice on (y, x)-plane that does not include any other characteristic quantity set, and said overlap number u is the difference subtracted said isolation number v from the total number of said characteristic quantity sets;

wherein calculated isolation number v and overlap number u are used as parameters for diagnosis of a condition of a heart of a patient.

8. A computer-implemented diagnostic program, comprising:
a first step of detecting R-R intervals of the electrocardiogram data collected for a predetermined time interval to generate a time-series data;
a second step of generating a series of partial sets B(j)'s, each of which contains n successive elements starting from the j-th element of said time-series data, wherein n is a constant integer smaller than the total number of elements in said time-series data;
a third step of calculating, using a computer, a set of characteristic quantities $(y_j, x_j)$ for each partial set B(j)

wherein $y_j$ is the mean value of all elements in the set B(j) and $x_j$ is the mean value of each difference of the first element from each element in the partial set B(j); and a fourth step of calculating, using a computer, an isolation number v, an overlap number u and a maximum overlap degree w as parameters for diagnosis after splitting (y, x)-plane into lattices, wherein said isolation number v is the number of said characteristic quantity sets each of which is included in a lattice on (y, x)-plane that does not include any other characteristic quantity set, said overlap number u is the difference subtracted said isolation number v from the total number of said characteristic quantity sets, and said maximum overlap degree w is the maximum number of characteristic quantity sets included in a lattice on said (y, x)-plane;

wherein calculated isolation number v, overlap number u and maximum overlap degree w are used as parameters for diagnosis of a condition of a heart of a patient.

9. A computer-implemented diagnostic program, comprising:
a first step of detecting R-R intervals of the electrocardiogram data collected for a predetermined time interval to generate a time-series data;
a second step of generating a series of partial sets B(j)'s, each of which contains n successive elements starting from the j-th element of said time-series data, wherein n is a constant integer smaller than the total number of elements in said time-series data;
a third step of calculating, using a computer, a set of characteristic quantities ($y_j$, $x_j$) for each partial set B (j) wherein $y_j$ is the mean value of all elements in the set B (j) and $x_j$ is the mean value of each difference of the first element from each element in the partial set B (j);
a fourth step of calculating, using a computer, an isolation number v, an overlap number u and a maximum overlap degree w after splitting (y, x)-plane into lattices, wherein said isolation number v is the number of said characteristic quantity sets each of which is included in a lattice on (y, x)-plane that does not include any other characteristic quantity set, said overlap number u is the difference subtracted said isolation number v from the total number of said characteristic quantity sets, and said maximum overlap degree w is the maximum number of characteristic quantity sets included in a lattice on said (y, x)-plane; and
a fifth step of calculating, using a computer, a index of heart condition μ as a parameter for diagnosis according to the formula μ=10*v/(u*w), wherein v is said isolation number, u is said overlap number, and w is said maximum overlap degree;
wherein said index of heart condition is used to diagnose a condition of a heart of a patient.

10. A computer-implemented diagnostic parameter calculation method for performing diagnosis by utilizing a diagnostic system including a network, a center equipment and one or more terminal equipments connected to said center equipment via the network, wherein each of said terminal equipment comprises an electrocardiograph, a data collection means for collecting the electrocardiogram data measured by said electrocardiograph and editing the sending data for said center equipment, and a communication interface with said network, and wherein said center equipment comprises a communication interface for receiving the data sent from each said terminal equipment via said network and a recording means for recording the data received with said communication interface, said diagnostic parameter calculation method comprising the steps of:
collecting digital electrocardiogram data during a predetermined time interval;
detecting R-R intervals of the electrocardiogram data to generate a time-series data;
generating a series of partial sets B(j)'s, each of which contains n successive elements starting from the j-th element of said time-series data, wherein n is a constant integer smaller than the total number of elements in said time-series data;
calculating, using a computer, a set of characteristic quantities (yj, xj) for each partial set B(j) wherein yj is the mean value of all elements in the set B(j) and xj is the mean value of each difference of the first element from each element in the partial set B(j); and
calculating, using a computer, an isolation number v and an overlap number u as parameters for diagnosis after splitting (y, x)-plane into lattices, wherein said isolation number v is the number of said characteristic quantity sets each of characteristic quantity set, and said overlap number u is the difference subtracted said isolation number v from the total number of said characteristic quantity sets;
diagnosing a condition of a heart of a patient based at least in part on the values of calculated isolation number v and overlap number u.

11. The diagnostic parameter calculation method as set forth in claim 10, further comprising the step of:
calculating, using a computer, a maximum overlap degree w as an additional parameter for diagnosis after splitting (y, x)-plane into lattices, wherein said maximum overlap degree w is the maximum number of characteristic quantity sets included in a lattice on said (y, x)-plane;
diagnosing a condition of a heart of a patient based at least in part on the values of calculated maximum overlap degree w.

12. The diagnostic parameter calculation method as set forth in claim 11, further comprising the step of:
calculating, using a computer, an index of heart condition μ as a parameter for diagnosis according to the formula μ=10*v/(u*w), wherein v is said isolation number, μ is said overlap number, and w is said maximum overlap degree;
diagnosing a condition of a heart of a patient based at least in part on the values of said index of heart condition.

13. A non-transitory computer readable medium having stored thereon computer executable instructions for carrying out the steps of the computer-implemented diagnostic program of claim 7.

14. A non-transitory computer readable medium having stored thereon computer executable instructions for carrying out the steps of the computer-implemented diagnostic program of claim 8.

15. A non-transitory computer readable medium having stored thereon computer executable instructions for carrying out the steps of the computer-implemented diagnostic program of claim 9.

16. A non-transitory computer readable medium having stored thereon computer executable instructions for carrying out the steps of claim 10.

17. A non-transitory computer readable medium having stored thereon computer executable instructions for carrying out the steps of claim 11.

18. A non-transitory computer readable medium having stored thereon computer executable instructions for carrying out the steps of claim 12.

19. A diagnostic system, comprising:
one or more terminal equipment connected to a network, each of said one or more terminal equipment including:
a electrocardiograph;
a data collection unit configured to collect the electrocardiogram data measured by said electrocardiograph and editing data to be sent; and
a communication interface configured to send data via said network; and
a center equipment connected to said one or more terminal equipment via said network, said center equipment including:
a communication interface configured to receive the data sent from each of said one or more terminal equipment via said network;
a recording unit configured to record the data received with said communication interface;
a R-R interval detecting unit configured to detect R-R intervals of the electrocardiogram data to generate a time-series data;
a characteristic quantity calculating unit configured to generate a series of partial sets B(j)'s, each of which contains n successive elements starting from the j-th element of said time-series data, wherein n is a constant integer smaller than the total number of elements in said time-series data, and calculating a set of characteristic quantities $(y_j, x_j)$ for each partial set B(j) wherein $y_j$ is the mean value of all elements in the set B(j) and $x_j$ is the mean value of each difference of the first element from each element in the partial set B(j); and
a diagnostic parameter calculation unit configured to calculate an isolation number v and an overlap number u as parameters for diagnosis after splitting (y, x)-plane into lattices, wherein said isolation number v is the number of said characteristic quantity sets each of which is included in a lattice on (y, x)-plane that does not include any other characteristic quantity set, and said overlap number u is the difference subtracted said isolation number v from the total number of said characteristic quantity sets;
wherein calculated isolation number v and overlap number u are parameters for diagnosis of a condition of a heart of a patient.

20. The diagnostic system of claim 19,
wherein said diagnostic parameter calculation unit is also configured to calculate a maximum overlap degree w as a parameter for diagnosis after splitting (y, x)-plane into lattices;
wherein said maximum overlap degree w is the maximum number of characteristic quantity sets included in a lattice on said (y, x)-plane; and
wherein maximum overlap degree w is also a parameter for diagnosis of a condition of a heart of a patient.

21. The diagnostic system of claim 20,
wherein said diagnostic parameter calculation unit is also configured to calculate a index of heart condition μ as a parameter for diagnosis according to the formula μ=10*v/(u*w), wherein v is said isolation number, u is said overlap number, and w is said maximum overlap degree;
wherein said index of heart condition is a parameter for diagnosis of a condition of a heart of a patient.

\* \* \* \* \*